(12) United States Patent
Rich et al.

(10) Patent No.: US 6,631,717 B1
(45) Date of Patent: Oct. 14, 2003

(54) RE-BREATHING APPARATUS FOR NON-INVASIVE CARDIAC OUTPUT, METHOD OF OPERATION, AND VENTILATOR CIRCUIT SO EQUIPPED

(75) Inventors: David R. Rich, Glastonbury, CT (US); Michael B. Jaffe, Cheshire, CT (US)

(73) Assignee: NTC Technology Inc., Wilmington, DE (US)

( * ) Notice: Subject to any disclaimer, the term of this patent is extended or adjusted under 35 U.S.C. 154(b) by 0 days.

(21) Appl. No.: 09/425,839

(22) Filed: Oct. 21, 1999

(65) Prior Publication Data (65)

(51) Int. Cl.[7] .................................................. A62B 7/00
(52) U.S. Cl. ............................. 128/205.13; 128/204.18
(58) Field of Search ...................... 128/204.18, 204.21, 128/204.24, 204.25, 204.27, 204.28, 205.11, 205.13, 205.14–205.17, 205.18, 207.14, 912, 200.24, 201.27

(56) References Cited

U.S. PATENT DOCUMENTS

| | | | | | |
|---|---|---|---|---|---|
| 514,448 | A | * | 2/1894 | Desant | 128/205.18 |
| 667,840 | A | * | 2/1901 | Guthrie | 128/202.13 |
| 1,213,302 | A | * | 1/1917 | Tullar | 128/205.18 |
| 2,428,451 | A | * | 10/1947 | Emerson | 128/205.13 |
| RE25,871 | E | * | 10/1965 | Andreasen | 128/204.28 |
| 3,789,837 | A | * | 2/1974 | Philips et al. | 128/202.22 |
| 3,910,261 | A | | 10/1975 | Ragsdale et al. | |
| 4,192,301 | A | | 3/1980 | Hardwick | |
| 4,239,038 | A | | 12/1980 | Holmes | |
| 4,267,827 | A | * | 5/1981 | Rauscher et al. | 128/205.15 |
| 4,340,044 | A | * | 7/1982 | Levy et al. | 128/204.21 |
| 4,932,401 | A | * | 6/1990 | Perkins | 128/203.12 |
| 4,934,360 | A | * | 6/1990 | Heilbron et al. | 128/205.13 |
| 4,941,476 | A | | 7/1990 | Fisher | |
| 4,947,860 | A | | 8/1990 | Fisher | |
| 5,299,579 | A | | 4/1994 | Gedeon et al. | |
| 5,509,406 | A | * | 4/1996 | Kock et al. | 128/200.24 |
| 5,642,726 | A | | 7/1997 | Owens et al. | |
| 5,664,563 | A | | 9/1997 | Schroeder et al. | |
| 5,678,540 | A | * | 10/1997 | Kock et al. | 128/205.13 |
| 5,683,232 | A | * | 11/1997 | Adahan | 128/204.18 |
| 5,769,072 | A | * | 6/1998 | Olsson et al. | 128/204.22 |
| 5,789,660 | A | * | 8/1998 | Kofoed et al. | 422/84 |
| 5,979,443 | A | * | 11/1999 | Dingley | 128/204.26 |
| 6,044,843 | A | * | 4/2000 | O'Neil et al. | 128/204.23 |
| 6,095,986 | A | * | 8/2000 | Braig et al. | 128/204.23 |
| 6,142,148 | A | * | 11/2000 | Weckstrom et al. | 128/204.22 |
| 6,283,120 | B1 | * | 9/2001 | Kellon | 128/204.26 |

FOREIGN PATENT DOCUMENTS

WO    WO 98/12963    9/1996

OTHER PUBLICATIONS

Blomqvist, H., et al., *A Non–Invasive Technique for Measurement of Lung Perfusion*, Intensive Care Medicine, 1986, 12:172.

(List continued on next page.)

*Primary Examiner*—Weilun Lo
*Assistant Examiner*—Teena Mitchell
(74) *Attorney, Agent, or Firm*—TraskBritt

(57) ABSTRACT

A re-breathing apparatus including a novel dual chamber reservoir connected to a ventilator circuit by means of a diverting adapter. The dual chamber reservoir utilizes two gas chambers which can be operated in reciprocating fashion. To accomplish re-breathing, expired gas is drawn into one chamber, while gas is ejected from the other chamber. The expired gas is then ejected into the breathing circuit as the patient inspires, while a charge of fresh gas is drawn into the other chamber. The diverting adaptor minimizes mixing of gases being drawn into and ejected from the two chambers. An advantage of the inventive method is that the total volume of gases in the system can be kept constant throughout re-breathing. The preferred embodiment of the inventive reservoir is a one-piece, blow-molded plastic, bellows-like structure which can be manufactured simply and inexpensively for one-time (disposable) use. Actuation of the system may be performed under microprocessor control.

41 Claims, 11 Drawing Sheets

OTHER PUBLICATIONS

Bosman, R.J., et al., *Non–invasive pulmonary blood flow measurement by means of $CO_2$ analysis of expiratory gases*, Intensive Care Med (1991) 17:98–102.

Capek, J.M., *Noninvasive Measurement of Cardiac Output Using Partial $CO_2$ Rebreathing* [Dissertation], Rensselaer Polytechnic Institute (1988), pp. 127–132.

Capek, John M., et al., *Noninvasive Measurement of Cardiac Output Using Partial $CO_2$ Rebreathing*, IEEE Transactions on Biomedical Engineering, vol. 35, No. 9, Sep. 1988, pp. 653–661.

de Abreu, M. Gama, et al., *Reliability of the Partial $CO_2$ Rebreathing Technique for Measurement of Cardiac Output*, Proceedings RC IEEE–EMBS & 14th BMESI—1995 (3 pages).

de Abreu, Marcelo Gama, et al., *Partial carbon dioxide rebreathing: A reliable technique for noninvasive measurement of nonshunted pulmonary capillary blood flow*, Crit Care Med 1997 vol. 25, No. 4, pp. 675–683.

de Abreu, Marcelo Gama, et al., *Measurement of Pulmonary Capillary Blood Flow for Trending Mixed Venous Blood Oxygen Saturation and Oxygen Delivery*, Crit. Care Med. (1998), vol. 26, No. 1 (Suppl.), A106, Abstract #238, (1 page).

de Abreu, Marcelo Gama, et al., *Is the Partial $CO_2$ Rebreathing Technique a Useful Tool for Trending Pulmonary Capillary Blood Flow During Adjustments of Peep?*, Crit. Care Med. (1998), vol. 26, No. 1 (Suppl.), A106, Abstract #237, (1 page).

Gedeon, Andras, et al., *Noninvasive Cardiac Output Determined with a New Method Based on Gas Exchange Measurements and Carbon Dioxide Rebreathing: a Study in Animals/Pigs*, Journal of Clinical Monitoring, vol. 8, No. 4, Oct. 1992, pp. 267–278.

Gedeon, A., *A new method for noninvasive bedside determination of pulmonary blood flow*, Medical & Biological Engineering & Computing, Jul. 1980, pp. 411–418.

Gedeon, A., *Noninvasive Pulmonary Blood Flow for Optimal Peep*, ICOR AB, Ulvsundavägen 178 B, S–161 30 Bromma, Sweden, pp. 49–58.

Osterlund, B., et al., *A new method of using gas exchange measurements for the noninvasive determination of cardiac output: clinical experiences in adults following cardiac surgery*, Acta Anaesthesiologica Scandinavica 39 (1995), pp. 727–732.

Sackner, Marvin A., *Measurement of cardiac output by alveolar gas exchange*, Handbook of Physiology ~ The Respiratory System IV, Chapter 13: Pulmonary Capillary Blood Flow, pp. 233–255.

Winkler, Tilo, et al., *Pulmonary Capillary Blood Flow by Partial $CO_2$ Rebreathing: A Simulation Study Using a Bicompartmental Model of Gas Exchange*, Crit. Care Med. (1998), vol. 26, No. 1 (Suppl.), A105, Abstract #234, (1 page).

* cited by examiner

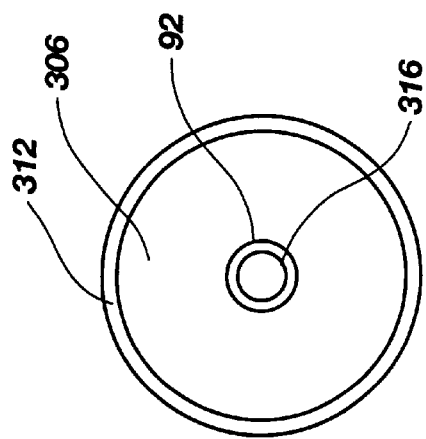
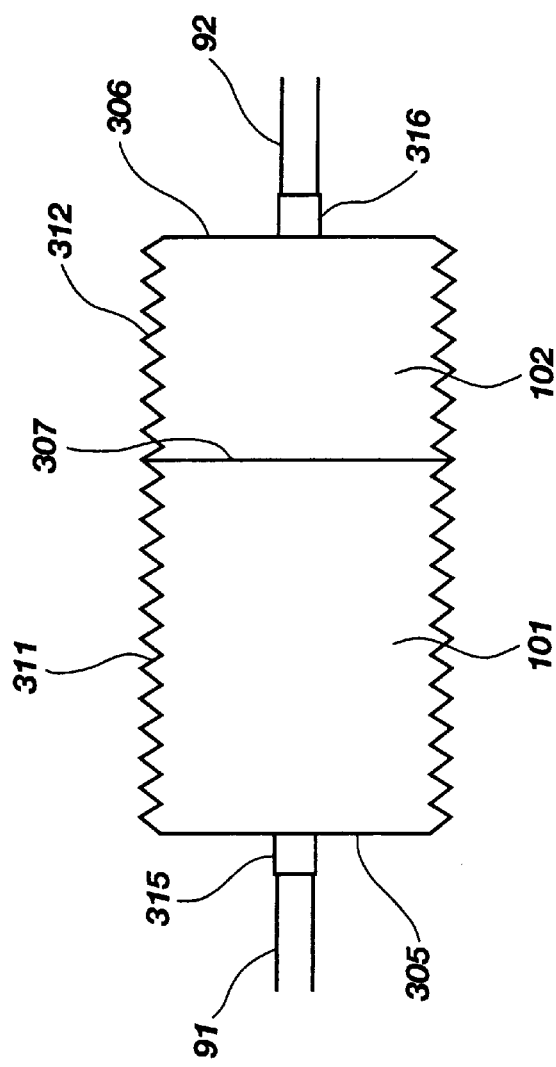
Fig. 3B
Fig. 3A

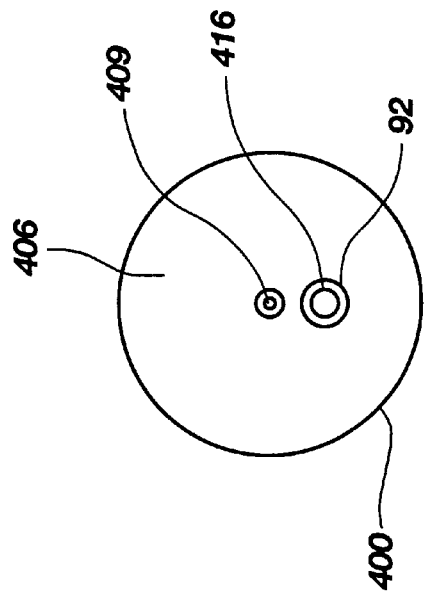
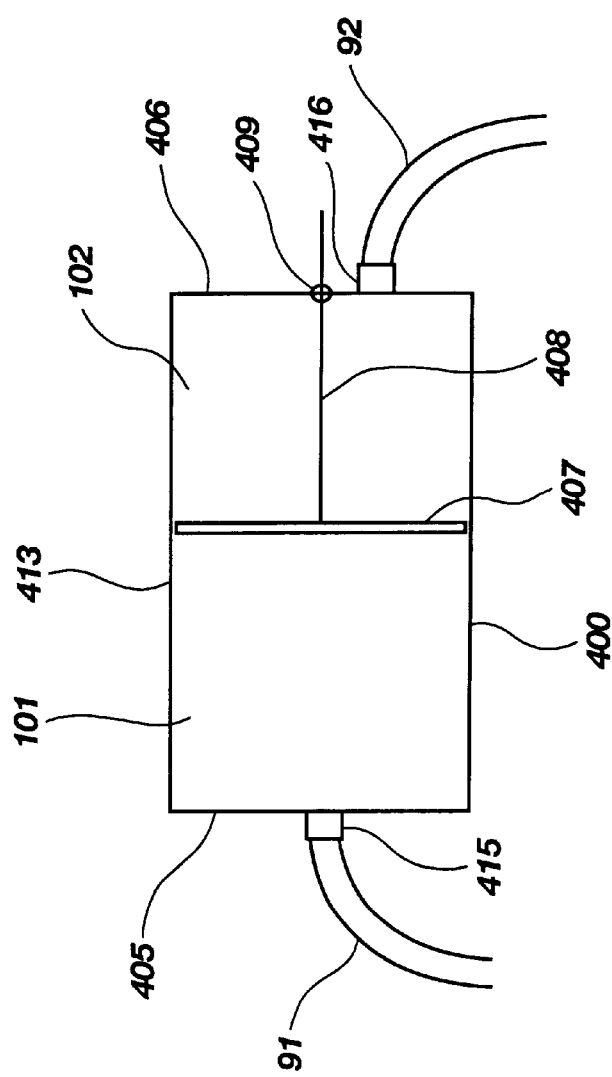
Fig. 4B
Fig. 4A

RE-BREATHING APPARATUS FOR NON-INVASIVE CARDIAC OUTPUT, METHOD OF OPERATION, AND VENTILATOR CIRCUIT SO EQUIPPED

BACKGROUND OF THE INVENTION

1. Field of the Invention

This invention relates to non-invasive approaches for determining cardiac output in patients, specifically to partial re-breathing techniques for determining cardiac output in patients, and most particularly to devices for storing and subsequently re-introducing into the ventilator circuit a volume of expired air in order to accomplish re-breathing, as well as ventilator circuits so equipped.

2. Statement of the Art

It is desirable, or even essential, to determine or monitor the cardiac output of a patient in many medical and surgical procedures. Invasive techniques well known and used in the art employ the use of catheters inserted at certain arterial points (e.g., femoral artery, jugular vein, etc.) to monitor blood temperature and pressure in order to determine cardiac output of the patient. Although capable of producing reasonably accurate results, the invasive nature of such procedures, with the attendant trauma and risk of infection, has demonstrated an unreasonably high potential for morbidity and mortality consequences.

Adolph Fick's measurement of cardiac output, first proposed in 1870, has served as the standard by which all other means of determining cardiac output have been evaluated since that date. Fick's well-known equation, written for $CO_2$, is:

$$Q = \frac{V_{CO_2}}{(C_{V_{CO_2}} - C_{A_{CO_2}})}$$

where Q is cardiac output, $V_{CO_2}$ is the amount of $CO_2$ excreted by the lungs and $C_{A_{CO2}}$ and $C_{V_{CO2}}$ are the arterial and venous $CO_2$ concentrations, respectively. Notably, the $CO_2$ Fick Equation usually presumes an invasive method (i.e., catheterization) of determining cardiac output because the arterial and mixed venous blood must be sampled in order to determine arterial and venous $CO_2$ concentrations.

It has previously been shown, however, that non-invasive techniques may be used for determining cardiac output while still using principles embodied in the Fick Equation. That is, expired $CO_2$ ("p$CO_2$") levels can be monitored to estimate arterial $CO_2$ concentrations and a varied form of the Fick Equation can be applied to evaluate observed changes in p$CO_2$ to estimate cardiac output. One use of the Fick Equation to determine cardiac output in non-invasive procedures requires the comparison of a "standard" ventilation event to a sudden change in ventilation which causes a change in expired $CO_2$ values and a change in excreted volume of $CO_2$. One commonly practiced means of providing a sudden change in effective ventilation is to cause the ventilated patient to re-breath a specified amount of previously exhaled air. This technique has commonly been called "re-breathing."

Prior methods of re-breathing have used the partial pressure of end-tidal $CO_2$ to approximate arterial $CO_2$ while the lungs act as a tonometer to measure venous $CO_2$. Such an approach to re-breathing has not proven to be satisfactory for determining cardiac output because the patient is required to breath directly into and from a closed volume in order to produce the necessary effect. However, it is usually very difficult for sedated or unconscious patients to actively participate in inhaling and exhaling into a bag. The work of some researchers has demonstrated that the Fick Equation could be further modified to eliminate the need to directly calculate venous $P_{CO_2}$ ($P_{VCO_2}$) by assuming that the $P_{VCO_2}$ does not change within the time period of the perturbation-an assumption that could be made by employing the partial re-breathing method. (See, Capek et al., "Noninvasive Measurement of Cardiac Output Using Partial $CO_2$ Rebreathing", IEEE Transactions On Biomedical Engineering, Vol. 35, No. 9, September 1988, pp. 653–661.)

Known partial re-breathing methods are advantageous over invasive measuring techniques because they 1) are non-invasive, 2) use the accepted Fick principle of calculation, 3) are easily automated, 4) require no patient cooperation and 5) allow cardiac output to be calculated from commonly monitored clinical signals. Thus, non-invasive cardiac output techniques are rapidly gaining favor. However, most known re-breathing circuits for storing expired air and then delivering it to the patient for partial re-breathing cause an increase in the volume and resistance of the respiratory path, which may complicate the operation of the ventilator. In addition, many conventional re-breathing circuits provide only a fixed re-breathing volume, which may not be optimum, or even suitable, for patients of various sizes and respiratory capacities. Finally, conventional re-breathing circuits frequently include components which are of complex and relatively expensive construction, making them contamination-prone, difficult to sterilize, and too expensive to be used as disposable units.

It would be advantageous to provide a re-breathing circuit which accomplishes re-breathing with little or no change to the respiratory path volume or air flow resistance, to minimize or eliminate interference with the ventilator function and reduce the load "seen" by the patient. It would also be advantageous to provide a re-breathing circuit in which re-breathing volumes can be varied as needed. It would be desirable for the re-breathing circuit to be usable with state-of-the art ventilator circuits and monitors without modification thereto. In many cases it is desirable for a re-breathing circuit to be made up of relatively simple and inexpensive, easy to fabricate, one-use (disposable) components.

BRIEF SUMMARY OF THE INVENTION

The present invention is a novel re-breathing apparatus suitable for use with a mechanically ventilated patient. The re-breathing apparatus includes a dual-chamber gas reservoir, each chamber of which is connected via tubing to a diverting adapter which allows flow of air to and from a respiration circuit. The total volume of the reservoir is fixed and the two chambers operate in reciprocal fashion, with one expanding to draw in air while the other is contracting to expel air. Accordingly, the total volume of gases in the reservoir, as well as in the respiration circuit as whole, can remain unchanged during operation of the apparatus in a re-breathing mode. The invented re-breathing apparatus thus has the advantage that it is entirely "invisible" in terms of operation of the respiration circuit, because there is no change in either the air volume or resistance to flow of the circuit (a factor which is of particular concern when a ventilator is used in the breathing circuit). A method of operating the re-breathing apparatus, the re-breathing apparatus and its components, and a respiration circuit including the inventive re-breathing apparatus are encompassed by the scope of the invention.

BRIEF DESCRIPTION OF THE SEVERAL VIEWS OF THE DRAWINGS

FIG. 3A illustrates the preferred embodiment of dual-chamber reservoir in cross section;

FIG. 3B is an end view of the embodiment of the invention shown in FIG. 3A;

FIG. 4A is a cross of an alternative embodiment of the dual-chamber reservoir;

FIG. 4B is an end view of the embodiment of the invention shown in FIG. 4A;

DETAILED DESCRIPTION OF THE INVENTION

Figure 1:
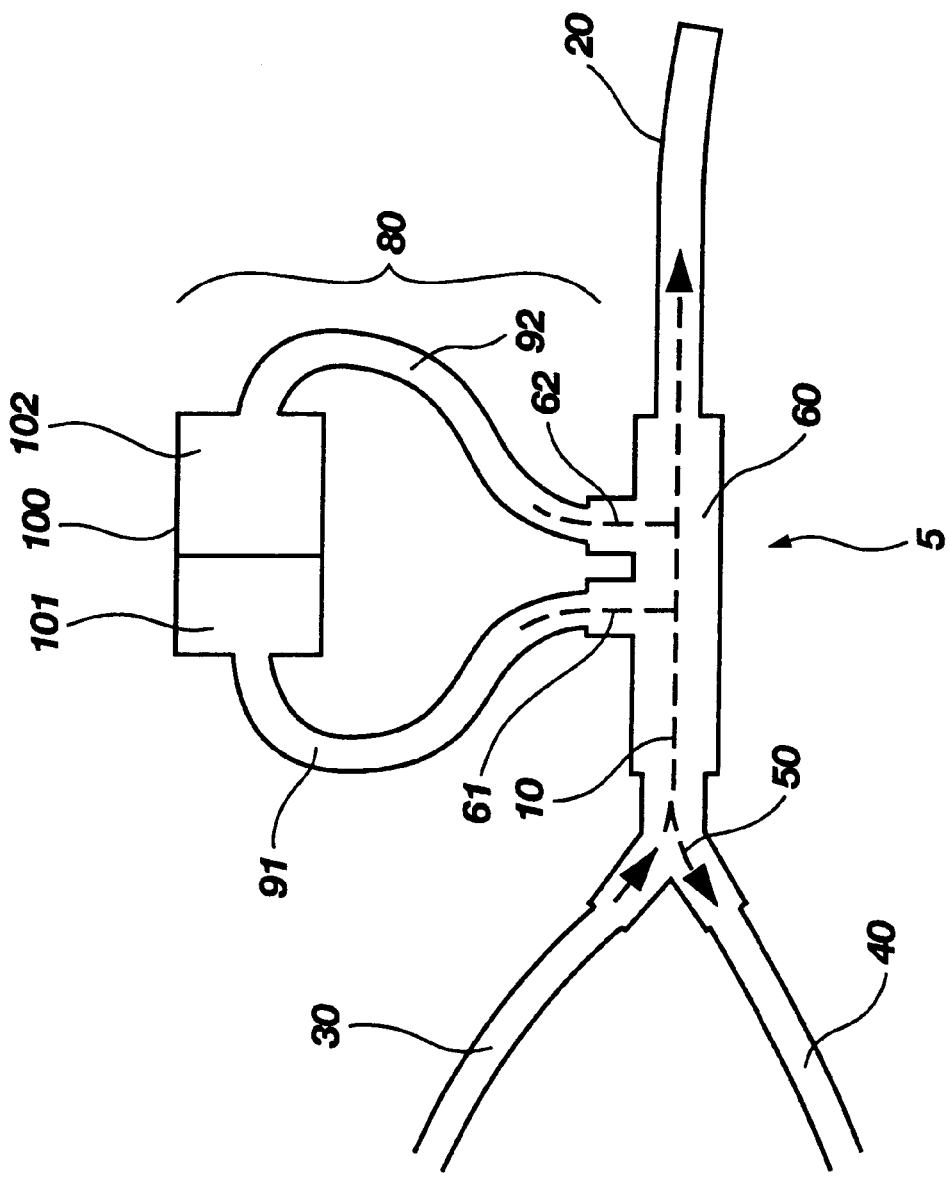
FIG. 1 is a schematic diagram of a ventilator circuit which incorporates the inventive re-breathing circuit.

FIG. 1 depicts the inventive re-breathing circuit 80 in relation to the respiration circuit as a whole, indicated generally at 5. Tubular airway 20 communicates air flow to and from the lungs of a patient. Tubular airway 20 may be placed in flow communication with the trachea of the patient (not shown) by known intubation processes, or by connection to a breathing mask positioned over the nose and/or mouth of the patient. During normal breathing (i.e., without re-breathing), fresh gas is provided to the patient from a ventilator or from the atmosphere via inspiratory hose 30, while expired gas is returned to the ventilator or vented to the atmosphere via expiratory hose 40. Y-piece 50 connects inspiratory hose 30 and expiratory hose 40 with diverting adapter 60, which is interposed between and in flow communication with tubular airway 20 and Y-piece 50. The primary respiratory path is indicated generally by broken lines at 10. The inventive re-breathing circuit, indicated generally at 80, is connected to the primary respiratory path 10 via diverting adapter 60. The inventive re-breathing circuit includes dual-chamber reservoir 100 (also referred to as reservoir 100), which includes a first chamber 101 and a second chamber 102 connected to diverting adapter 60 by hoses 91 and 92, respectively. In order to accomplish re-breathing, expired gases are drawn into chamber 102 of reservoir 100, and subsequently injected into the circuit during re-breathing. Chambers 101 and 102, or portions thereof, are compressed and expanded in a reciprocal fashion so that as one expands by a given volume, the other is compressed by the same volume, keeping the total volume of gas within the reservoir 100, and in the system 5 as a whole, constant.

The principle of operation of dual chamber reservoir 100 is described with reference to FIGS. 2A through 2D. FIGS. 2A through 2D depict a system which includes the presently preferred embodiment of the dual-chamber reservoir 100; however, the basic principal of operation is the same for all embodiments of the reservoir. During normal breathing when no re-breathing is desired, chamber 101 of reservoir 100 is held at its maximum volume, while chamber 102 of reservoir 100 is at its minimum volume, as shown in FIG. 2A. Fresh air, which is present in chamber 101 when it is expanded to its maximum volume state is stored in chamber 101 during normal ventilation. No air flows into or out of either chamber of the reservoir 100 during normal ventilation.

Figure 2B:
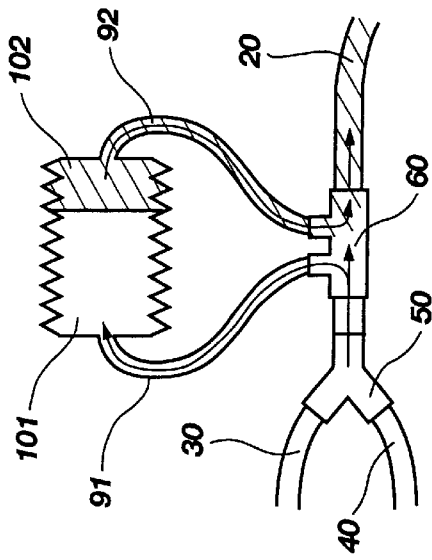
FIG. 2B depicts the expansion of chamber 102 and compression of chamber 101 of the dual-chamber reservoir, to store expired gases and eject fresh gases during the last expiratory breath prior to the start of re-breathing.
Figure 2D:
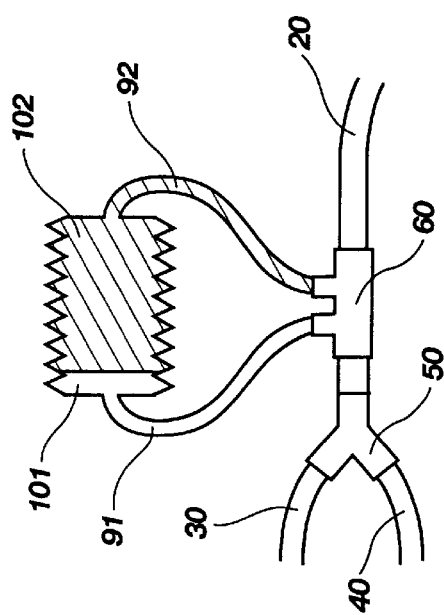
FIG. 2D shows the injection of expired gases stored in chamber 102 of the reservoir into the circuit during re-breathing, while fresh gas is simultaneously drawn into chamber 1.
Figure 2A:
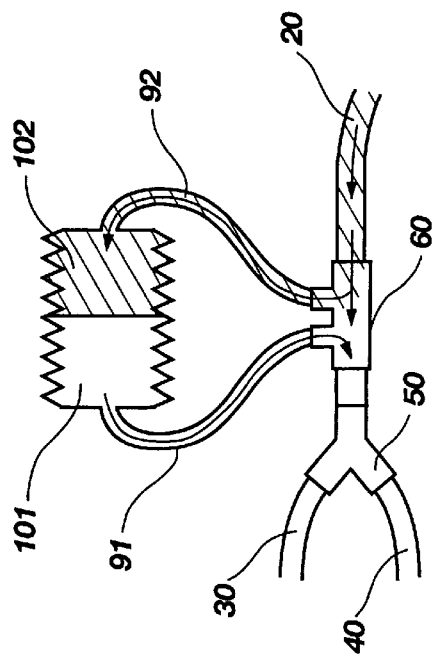
FIG. 2A shows the configuration of the preferred embodiment of the dual-chamber reservoir during normal ventilation without re-breathing.

As shown in FIG. 2B, during the last expiratory breath prior to the start of re-breathing, chamber 102 is caused to expand, drawing expired gases into the chamber 102 via tube 92, while chamber 101 contracts to inject the gases which were stored therein into the circuit via tube 91. Chamber 102 thus provides a reservoir for storing expired gas for re-breathing. Diverting adapter 60 provides for the injection of fresh gases from chamber 101 into circuit 5 at a point downstream (i.e. further from the patient) than the point at which expired gases are withdrawn into chamber 102. Diverting adapter 60 is designed to minimize mixing of fresh and expired gases in its interior during filling and emptying of the reservoir chambers.

Figure 2C:
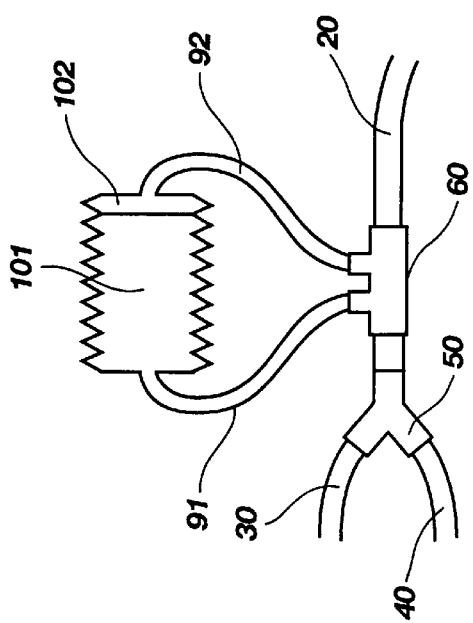
FIG. 2C shows the configuration of the dual-chamber reservoir at the end of the expiratory phase immediately prior to the start of re-breathing.

The expansion of chamber 102 (and simultaneous contraction of chamber 101) is completed by the end of the expiratory breath prior to the start of re-breathing, with the result that chamber 102 is "primed" to a desired volume with expired gases and prepared for the start of re-breathing to begin with the next breath, as shown in FIG. 2C, and chamber 101 is collapsed to a minimum volume commensurate with the expansion of chamber 102.

Timed with the ventilator inspiratory phase, chamber 102 is compressed to inject the expired gases stored therein into the circuit for re-breathing by the patient, as shown in FIG.

2D. Concurrently, chamber 101 is expanded to draw in fresh gases from inspiratory hose 30. In the steps shown in FIGS. 2A–2D, the volume of air withdrawn from the circuit 5 is always the same as the volume of air injected into the circuit 5, so no net accumulation or deficit of gases occurs in the circuit between inspiration and expiration, and operation of the re-breathing circuit is transparent to the ventilator and patient.

Figure 5:
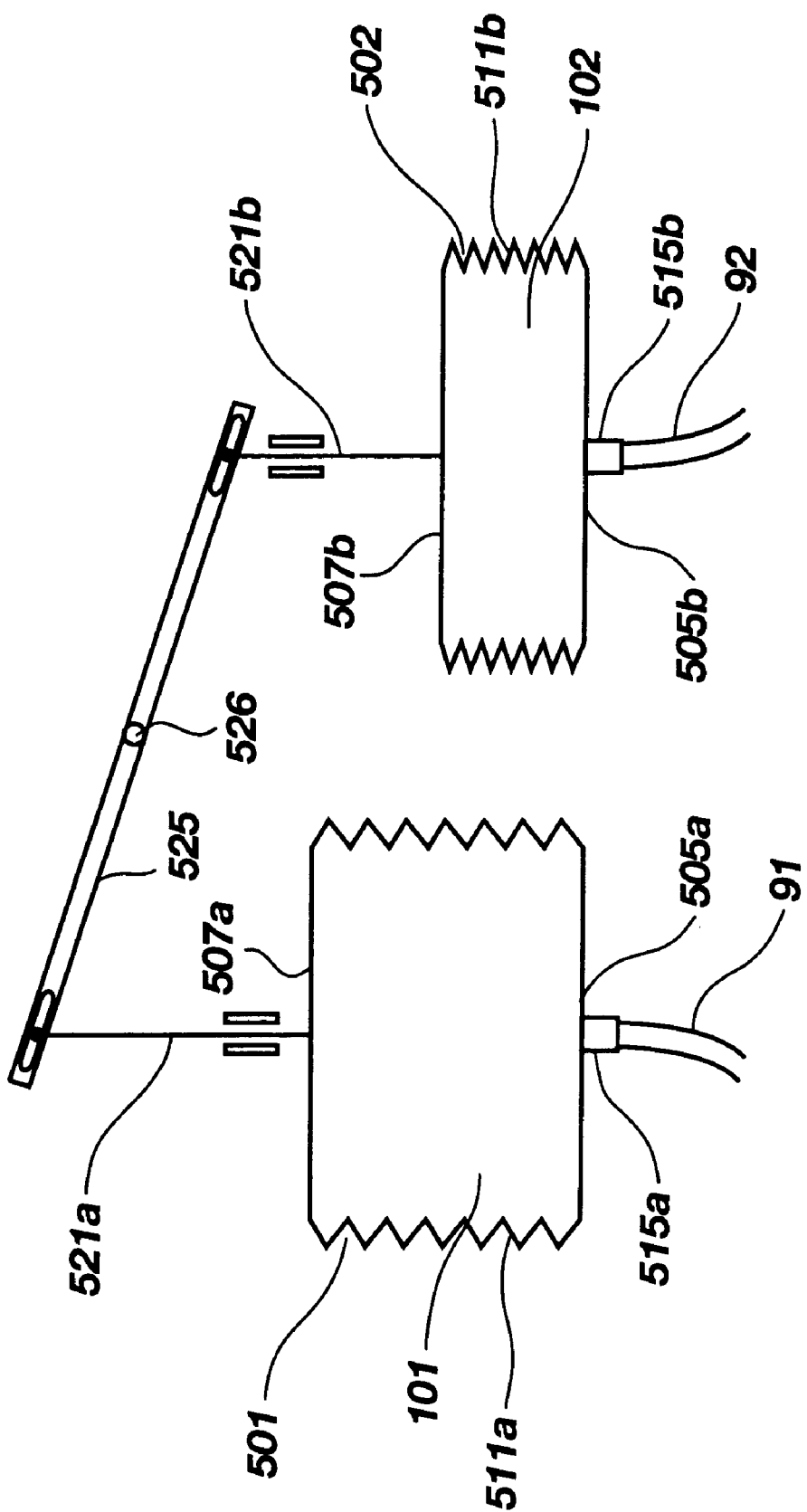
FIG. 5 illustrates a further alternative embodiment of the dual-chamber reservoir.
Figure 6:
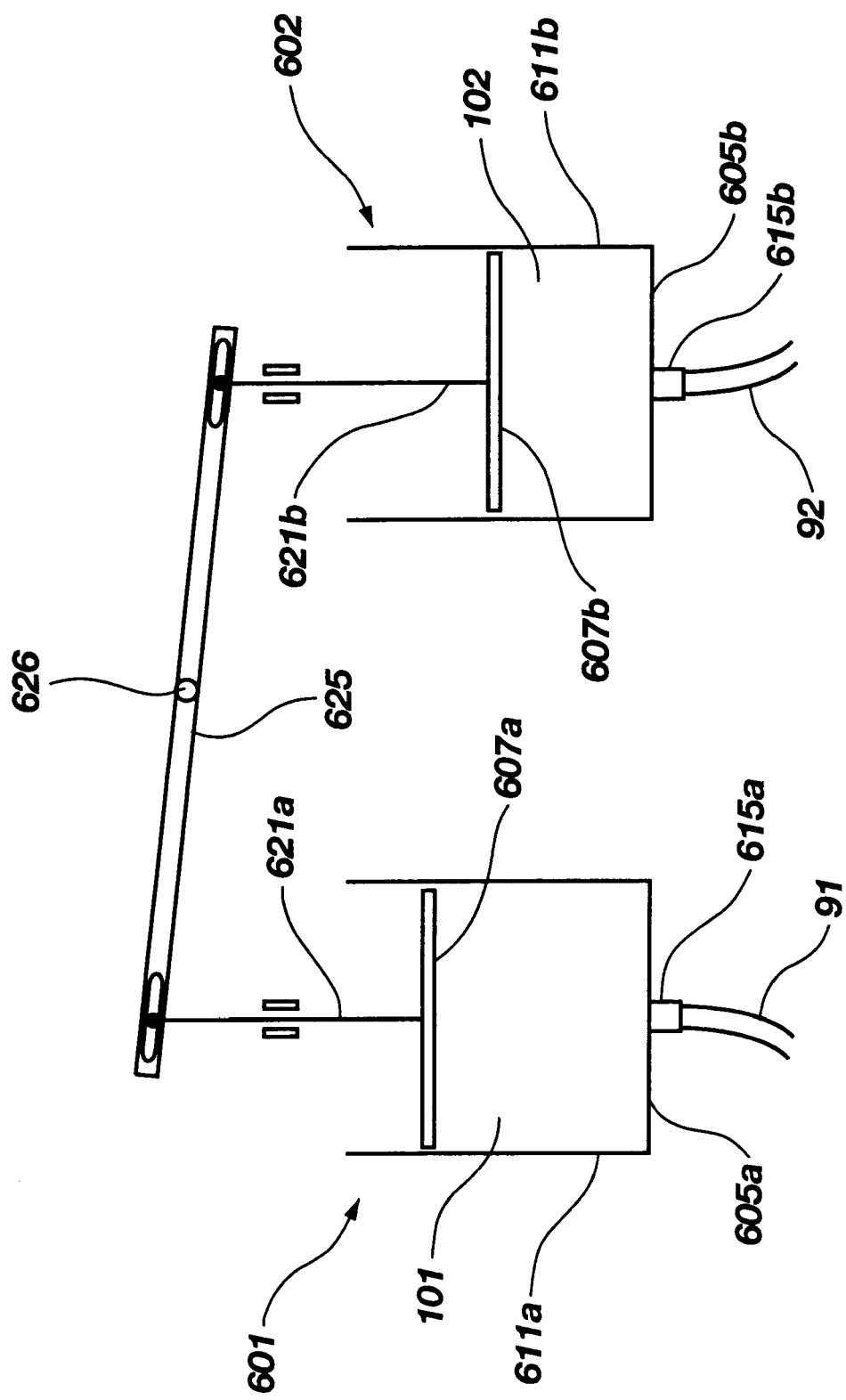
FIG. 6 illustrates a further alternative embodiment of the dual-chamber reservoir.
Figure 7:
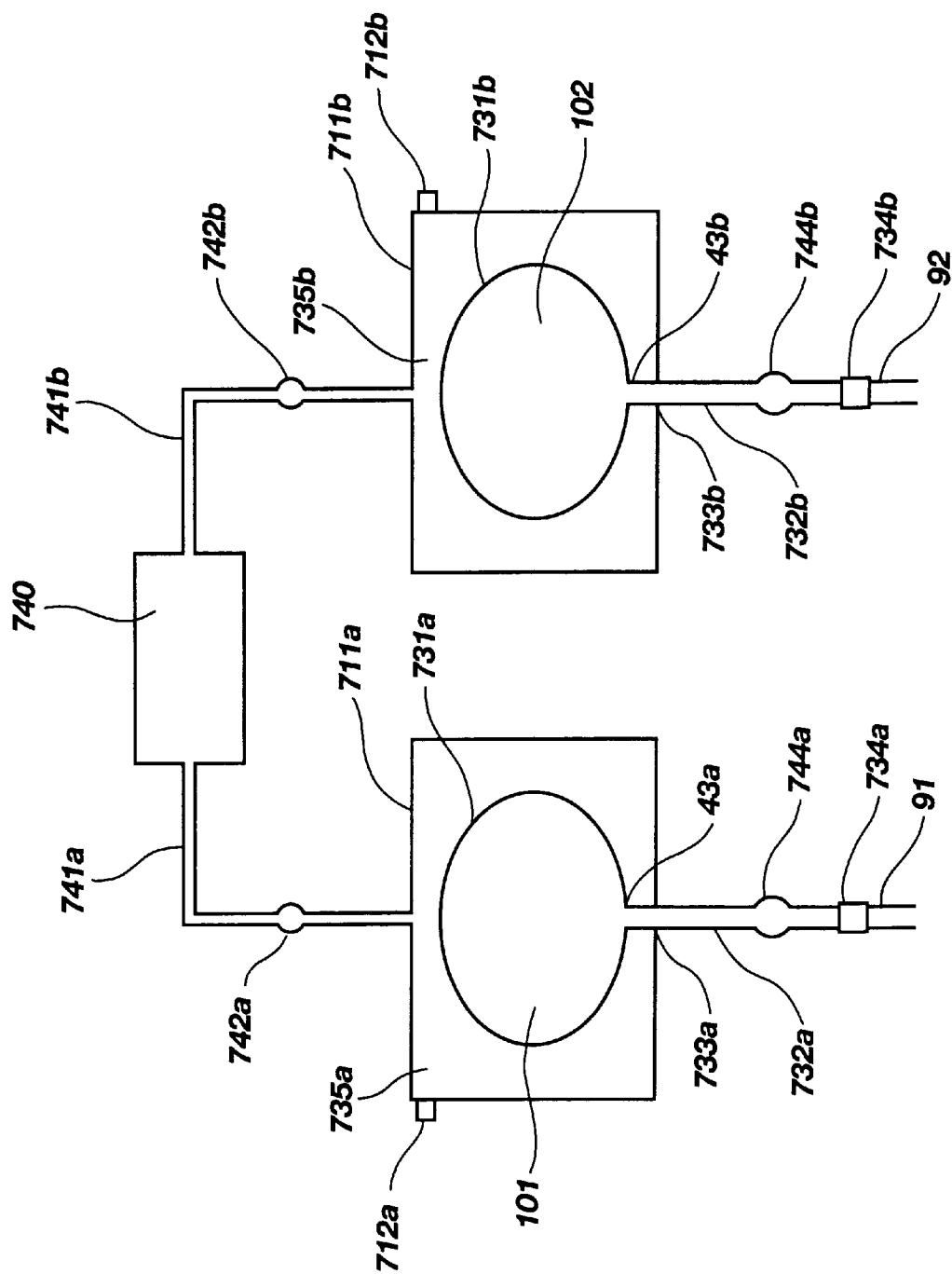
FIG. 7 illustrates a further alternative embodiment of the dual-chamber reservoir.
Figure 8A:
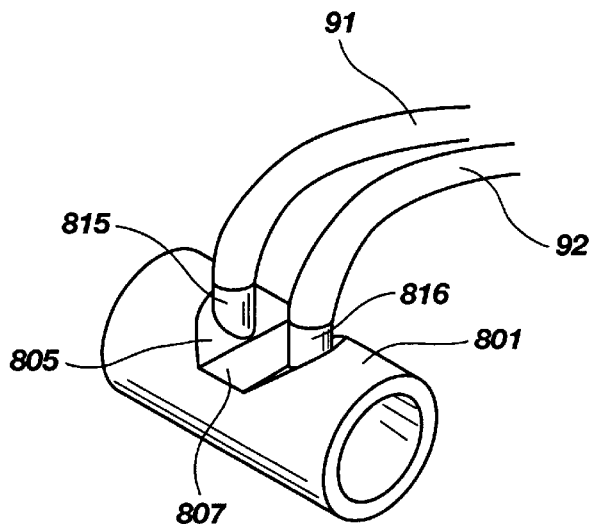
FIG. 8A illustrates the preferred embodiment of the diverting adapter.
Figure 8B:
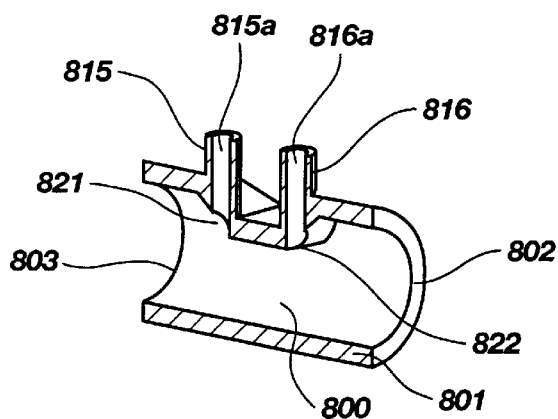
FIG. 8B is a cut-away view of the embodiment of the diverting adapter shown in FIG. 8A.
Figure 8C:
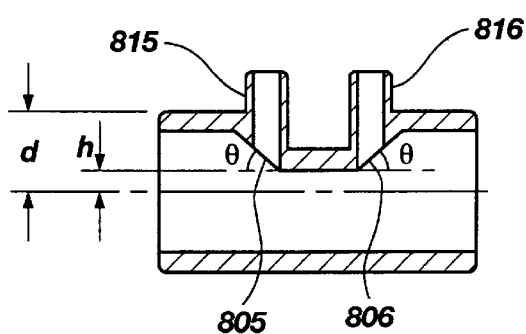
FIG. 8C is a longitudinal cross-sectional view of the embodiment of the diverting adapter shown in FIG. 8A.
Figure 8D:
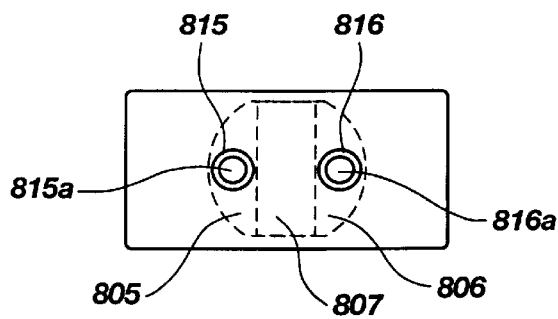
FIG. 8D is a further view of the embodiment of the diverting adapter shown in FIG. 8A.
Figure 9A:
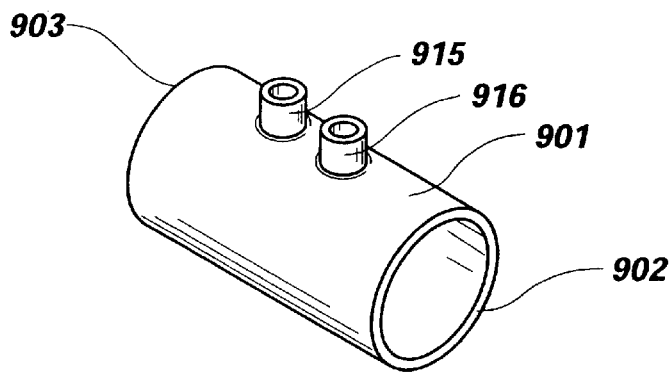
FIG. 9A illustrates an alternative embodiment of the diverting adapter.
Figure 9B:
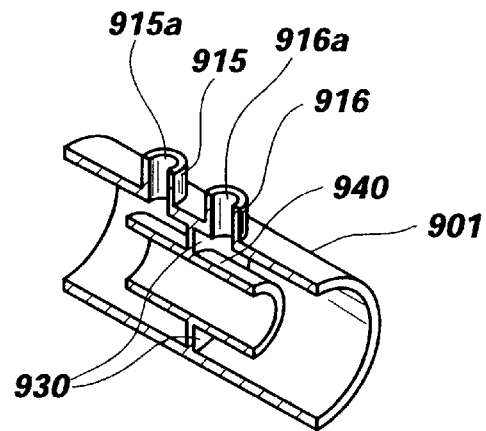
FIG. 9B is a cut-away view of the embodiment of the diverting adapter shown in FIG. 9A.
Figure 9C:
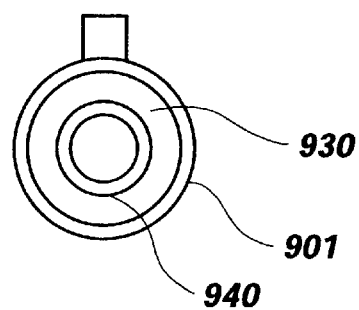
FIG. 9C is an end view of the embodiment of the diverting adapter shown in FIG. 9A.

The chambers may be directly mechanically coupled as in the bellows design of FIGS. 2A through 2D, 3, and 4, indirectly coupled through a mechanical linkage as in the designs of FIGS. 5, 6, and 7, or actuated separated but coupled via control logic. Specifically, if desired, the chambers used in the designs of FIGS. 5, 6, and 7 could be coupled via control logic rather than via the mechanical linkage shown in the figures. In the directly and indirectly mechanically coupled systems the amount of gas withdrawn from the system matches the amount of gas injected into the system at each moment. In a system with no mechanical coupling, it would be possible to modify the control logic to adjust the withdrawal and injection of gases such that the total quantities of gases withdrawn and injected from the system during a single breathing cycle were substantially equal, but that on a moment-by-moment basis, an imbalance could occur. This would lead to fluctuations in the pressure of the system, so it would be necessary to ensure that such pressure fluctuations remained within a range which would not interfere with ventilator function or patient respiration.

A presently preferred embodiment of dual-chamber reservoir 100 is shown in FIGS. 3A and 3B. It is a cylindrical, bellows-like structure with two flat, preferably circular end walls 305 and 306, and two chambers 101 and 102 separated by internal wall 307. The lengths of side wall 311 of chamber 101 and side wall 312 of chamber 102 can be varied to allow shortening or lengthening of each chamber 101 and 102 without changing the diameter of the chamber. Side wall 311 and side wall 312 are preferably accordion-pleated, but could also be helically pleated or otherwise configured to permit them to be collapsed and expanded (shortened or lengthened). A linear relationship between chamber length and volume will be obtained if shortening and lengthening occur without change in chamber cross-sectional area. However, there is no need for the volume change to be linear, in this and other embodiments of the invention. In any embodiment of the invention, the control algorithm must take into account the relationship between chamber actuation and change in chamber volume. Side walls 311 and 312 are preferably circular in cross section, but could also have another cross-sectional shape. Chamber 101 has an outlet 315 which is connected to tube 91 leading to diverting adapter 60. Chamber 102 has an outlet 316 which is connected to tube 92 leading to diverting adapter 60. Outlets 315 and 316 are depicted here at the ends of the chambers; however, any outlet location may be selected which does not interfere with expansion and contraction of the chambers. For example, if only a portion of the chamber wall was subject to expansion or contraction, the outlet could be placed on the chamber wall on the non-expanding and non-contracting portion. During use, end walls 305 and 306 are held at a fixed distance from each other, which distance defines the total volume of reservoir 100. Movement of internal wall 307 toward end wall 305 results in a decrease in the volume of chamber 101 and an increase in the volume of chamber 102, while movement of internal wall 307 toward end wall 306 results in an increase in the volume of chamber 101 and a decrease in the volume of chamber 102. The longitudinal distance between end walls 305 and 306 can be adjusted for each patient to provide the optimal total volume for reservoir 100. The distance moved by internal wall 307, which may also be adjusted for each patient, determines the actual volume of gas stored in and delivered by chamber 102 during re-breathing. The bellows structure shown in FIGS. 3A and 3B can be manufactured as a one piece blow-molded component, inexpensive enough to be disposable. Various actuation mechanisms might be used for moving internal wall 307, for example a linear stepper motor or a pneumatic, hydraulic, or solenoid-based mechanism. The practice of the invention is not limited to the particular actuation mechanism used. Actuation of internal wall 307 may be controlled by a programmed microprocessor, switches, or other means. The use of an actuator controlled by a microprocessor, in this and other embodiments of the invention, is particularly advantageous because it makes it possible for the volume of gases exchanged to be varied to tune the percent re-breathing for each patient, to take into account differences in tidal volume, physiological response, etc. Moreover, re-breathing could be under closed-loop control, if desired.

FIGS. 4A and 4B illustrates an alternative embodiment of the dual-chamber reservoir, which is a rigid-walled cylinder 400 which is formed by rigid side wall 413 and end walls 405 and 406. The interior of cylinder 400 is divided into chambers 101 and 102 by movable piston wall 407. Movable piston wall 407 forms a sliding, substantially gas-tight seal with side wall 413, to prevent the leakage of gases between chambers 101 and 102. This is achieved, as known in the art, by use of an O-ring or other annular seal structure around the periphery of movable piston wall 407. Movable piston wall 407 is driven by piston rod 408, which passes through opening 409 in end wall 406, the bore of opening 409 also being provided with a sliding seal. Gases enter and exit chamber 101 through outlet 415, to which is connected tube 91. Similarly, gases enter and exit chamber 102 through outlet 416, to which is connected tube 92. Shaft 408 may be driven by various mechanism, for example a linear stepper motor or a pneumatic, hydraulic, or solenoid-based mechanism. The practice of the invention is not limited to the particular actuation mechanism used. The drive mechanism may be controlled by various methods known in the art, including a programmed microprocessor, switches, and so forth.

FIG. 5 illustrates a further alternative embodiment of the dual-chamber reservoir, in which two separate bellows structures serve as chambers 101 and 102. The two bellows are preferably identical; in this illustration the components of each are numbered identically, distinguished by the letters "a" and "b". The first bellows 501, which contains inner chamber 101, includes a fixed end wall 505a, movable end wall 507a, and variable length side wall 511a. Gases enter and exit chamber 101 through outlet 515a in end wall 505a, which is connected to tube 91. The second bellows 502, which contains inner chamber 102, includes a fixed end wall 505b, movable end wall 507b, and variable length side wall 511b. Variable length side walls 511a and 511b are preferably accordion pleated, but may also be helically pleated or otherwise configured to permit chambers 101 and 102 to be collapsed and expanded (shortened and lengthened). Gases enter and exit chamber 102 through outlet 515b in end wall 505b, which is connected to tube 92. Linkage 521a is attached at its first end to movable end wall 507 a and attached at its second end to a first end of arm 525. Linkage 521b is attached at its first end to movable end wall 507b and attached at its second end to the second end of arm 525. Arm 525 is mounted on rotatable shaft 526; linkages 521a and 521*b* are driven in reciprocating fashion by arm 525 responsive to the direction of rotation of shaft 526. Shaft 526 is driven by, for example, a rotary two-way electric motor, or a motor or cylinder with a spring return, under switch or microprocessor control. Various actuation and control mechanisms can be used in the practice of the invention.

FIG. 6 illustrates a further alternative embodiment of the dual-chamber reservoir, in which two separate cylinders 601 and 602 contain as chambers 101 and 102. The two cylinders are preferably identical; in this illustration the components of each are numbered identically, distinguished by the letters "a" and "b". The first cylinder 601, which contains inner chamber 101, includes rigid side wall 611*a*, end wall 605*a*, and movable piston wall 607*a* driven by piston rod 621*a*. Gases enter and exit chamber 101 through outlet 615*a* in end wall 605*a*, which is connected to tube 91. The second cylinder 602, which contains inner chamber 102, includes rigid side wall 611*b*, end wall 605*b*, and moving piston wall 607*b* driven by piston rod 621*b*. Movable piston walls 607*a* and 607*b* form sliding, substantially gas-tight seals with rigid side walls 611*a* and 611*b*, respectively, by use of an O-ring or other annular seal structure on the periphery of each piston wall. Gases enter and exit chamber 102 through outlet 615*b* in end wall 605*b*, which is connected to tube 92. Piston rod 621*a* is attached at its first end to movable end wall 607*a* and attached at its second end to a first end of arm 625. Piston rod 621*b* is attached at its first end to movable end wall 607*b* and attached at its second end to the second end of arm 625. Arm 625 is mounted rotatable shaft 626; piston rods 621*a* and 621*b* are driven in reciprocating fashion by arm 625 responsive to the direction of rotation of shaft 626. Actuation and control of shaft 626 is as described above in connection with the embodiment of the invention shown in FIG. 5.

FIG. 7 illustrates a further alternative embodiment of the dual-chamber reservoir. In this embodiment, chamber 101 is provided within variable volume chamber 731*a* which in this example of the invention is a flexible, thin-walled bag 731*a*. The variable volume chamber 731*a* is contained within fixed volume chamber 711*a*. The volume of variable volume chamber 731*a* (and hence chamber 101) is controlled by adjusting the pressure in space 735*a* between variable volume chamber 731*a* and fixed volume chamber 711*a*. Similarly, chamber 102 is provided within variable volume chamber (e.g., a flexible, thin-walled bag) 731*b* which is contained within fixed volume chamber 711*b*. The volume of variable volume chamber 731*b* (and hence chamber 102) is controlled by adjusting the pressure in space 735*b* between variable volume chamber 731*b* and fixed volume chamber 711*b*. Vacuum pump or vacuum/positive pressure pump 740 is connected to space 735*a* by line 741*a*, and to space 735*b* by line 741*b*. For example, an increase in the volume of variable volume chamber 731*a* and decrease in the volume of variable volume chamber 731*b* is caused by generating a negative pressure (vacuum) in space 735*a* relative to the pressure in the variable volume chamber of bag 731*a*, while simultaneously generating a positive pressure in space 735*b* relative to the pressure in the interior of variable volume chamber 731*b*. Although flexible, thin-walled bags are used in the embodiment presented here, variable volume chambers 731*a* and 731*b* can be any structure which will expand or compress in response to a difference in external and internal pressure. As a further alternative, chambers 101 and 102 could be provided in spaces 735*a* and 735*b*, respectively, while the increases and decreases in pressure which drive gases in and out of chambers 101 and 102 could be produced by varying the volumes of bags 731*a* and 731*b*. Fixed volume chambers 711*a* and 711*b* may include pressure relief valves 712*a* and 712*b*, respectively. The pressure relief valves are used to permit contraction of variable volume chambers 731*a* and 731*b* by permitting release of a vacuum in space 735*a* and 735*b* in the case that only a vacuum pump 740 is used. Gauge/absolute pressure sensors 742*a* and 742*b* are placed in lines 741*a* and 741*b*, respectively to monitor pressures in chambers 711*a* and 711*b* to ensure proper reciprocal expansion and contraction of chambers 731*a* and 731*b*. In the present exemplary embodiment of the invention, outlet 43*a* of chamber 101 (variable volume chamber 731*a*) is connected to tube 732*a*. Tube 732*a* passes through opening 733*a* in the wall of fixed volume chamber 711*a*. Opening 733*a* is sealed to the exterior of tube 732*a* to prevent the flow of air or gases into or out of space 735*a* at opening 733*a*. Tube 732*a* is joined to tube 91 at connector 734*a*. Flow sensor 744*a* is included on tube 732*a*. Similarly, outlet 43*b* of variable volume chamber 731*b* may be connected to tube 732*b*, which passes through opening 733*b* in the wall of fixed volume chamber 711*b*. Opening 733*b* is sealed to the exterior of tube 732*b*. Tube 732*b* is connected to tube 92 at connector 734*b*, and a flow sensor 744*b* may be included on tube 732*b*. In general, each variable volume chamber communicates with the main breathing circuit through a tubular element connected to the outlet of the variable volume chamber and passing through the wall of the fixed volume chamber with an air-tight seal between the tube and the wall of the fixed volume chamber. In the example presented here, the tubular elements are made up of the tube 732*a* and tube 91, and tube 732*b* and tube 92. It will be appreciated by one of ordinary skill in the art that it would be possible to use various combinations of tubes and connectors, and that the invention is not limited to the particular arrangement of tubes and connectors presented here.

It will be appreciated that various mechanisms can be devised for controlling the volumes of the two chambers of the different embodiments, and that actuation of the mechanism can be microprocessor-controlled if desired. In general, the volumes of the chambers are controlled by controlling the pressures in spaces 735*a* and 735*b*, through generation of a vacuum or positive pressure with vacuum pump or vacuum/positive pressure pump 740 and/or release of pressure through pressure relief valves 712*a* and 712*b*. Accordingly, pump 740 and pressure relief valves 712*a* and 712*b* could be microprocessor controlled, while flow sensor and Gauge/absolute pressure sensors could be used to provide feedback signals. The invention is not limited to the use of a particular actuation mechanism or control scheme.

A presently preferred embodiment of the diverting adapter 60 is shown in FIGS. 8A through 8D. In general, as shown in FIG. 1, diverting adapter 60 includes a main flow passage which is an integral part of primary respiratory path 10, and two diverting passages 61 and 62, which provide for the flow of gases between main the flow passage of the adaptor and chambers 101 and 102 of dual chamber reservoir 100. The main flow passage of the adaptor is positioned in primary respiratory path 10, between tubular airway 20 and Y-piece 50, as shown in FIG. 1. Referring now to FIGS. 8A through 8D, cylindrical element 801, which defines main flow passage 800, has a diameter d. First end 802 and second end 803 of cylindrical element 801 are connected to Y-piece 50 and tubular airway 20, respectively, by, for example, an adhesive or thermal welding. Tube 91 from chamber 101 of the dual-chamber reservoir 100 is connected to first tube connector 815, while tube 92 from chamber 102 is connected to second tube connector 816. In this preferred embodiment of the invention, the first diverting passage runs through first tube connector 815 and is continuous with tube 91, while the second diverting passage runs through second tube connector 816 and is continuous with tube 92. Although it is preferred to have tubes connecting between diverting adapter 60 and the chambers of dual chamber reservoir 100, to allow the reservoir to be placed at a variable distance from the breathing circuit, in an alternative embodiment it would be possible for diverting adapter 60 to be connected directly to the chambers of dual chamber reservoir 100. Tube connectors 815 and 816 are preferably substantially parallel to each other and substantially perpendicular to the longitudinal axis of cylindrical element 801, with tube connector 816 on the upstream side of tube connector 815 (i.e., on the side closer to the patient). First tube connector 815 defining first bore 815 a joins to first angled wall region 805. First angled wall region 805 is planar and intersects cylindrical element 801 at an angle relative to the longitudinal axis of cylindrical element 801. First angled wall region 805 also intersects a planar section 807 which is parallel to the longitudinal axis of cylindrical element 801 and substantially perpendicular to tube connectors 815 and 816. Planar section 807 is rectangular and intersects cylindrical element 801 along its edges parallel to the longitudinal axis of cylindrical element 801. Planar section 807 is located at a distance h from the longitudinal axis of cylindrical element 801; distance h is always less than d. Second tube connector 816 defining second bore 816 a joins to second angled wall region 806, which is planar and intersects cylindrical element 801 at an angle $\theta$ relative to the longitudinal axis of cylindrical element 801. Second angled wall region 806 also intersects planar section 807. The lines of intersection between planar section 807 and angled wall regions 805 and 806 are perpendicular to the long axis of cylindrical element 801. The end of tube 815 is flush with first angled wall region 805, with the effect that the upstream edge of opening 821 of tube connector 815 extends further into primary passage 800. Conversely, because the end of tube connector 816 is flush with angled wall region 806, the downstream edge of opening 822 of tube connector 816 extends further into primary passage 800. The orientations of angled wall regions 805 and 806, and openings 821 and 822 therein, serve to minimize the mixing of fresh and expired gases as they flow into and out of chambers 101 and 102 of reservoir 100. An advantage of the combination of the inventive reservoir system and diverting adapter is that in the event of a malfunction which causes the reservoir system to stop functioning, gas will still be able to flow from the ventilator to the patient, through the diverting adapter. In prior art systems which use a valve to divert gases to be stored for re-breathing, a malfunction of the valve could block the flow of gases between the ventilator and the patient.

Alternative embodiments of diverting adapter 60 are shown in FIGS. 9A–11C. In the embodiment of diverting adapter 60 shown in FIGS. 9A–9C, tube connectors 915 and 916 connect to and have bores 915a and 916a which have openings flush with the outer wall of cylindrical element 901 having first end 902 and second end 903. The primary respiratory path 10 is through primary flow tube 940, which is preferably co-axial with cylindrical element 901. Primary flow tube 940 is supported by annular support element 930, which is connected at its periphery to the interior of cylindrical element 901, substantially perpendicular to the longitudinal axis of cylindrical element 901 and midway between tube connectors 915 and 916. During normal breathing or ventilation, gas flows through primary flow tube 940. During re-breathing, gas flows through the space between cylindrical element 901 and primary flow tube 940, on either side of annular support element 930, and then through either tube connector 915 or tube connector 916. Annular support element 930 prevents mixing of the gases flowing through tube connectors 915 and 916.

Figure 10A:
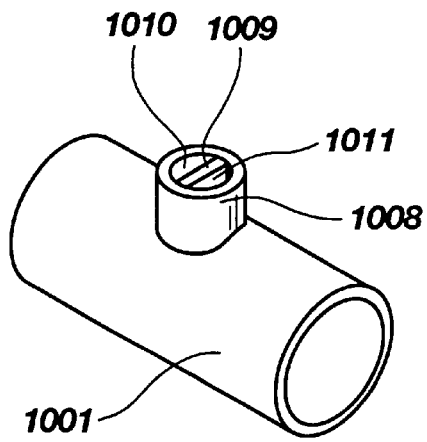
FIG. 10A illustrates a further alternative embodiment of the diverting adapter.
Figure 10B:
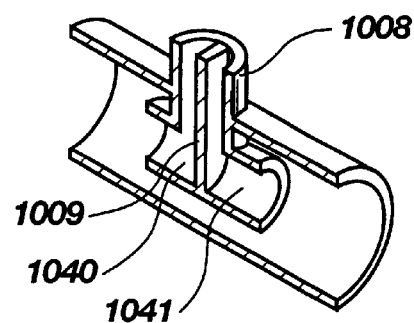
FIG. 10B is a cut-away view of the embodiment of the diverting adapter shown in FIG. 10A.
Figure 10C:
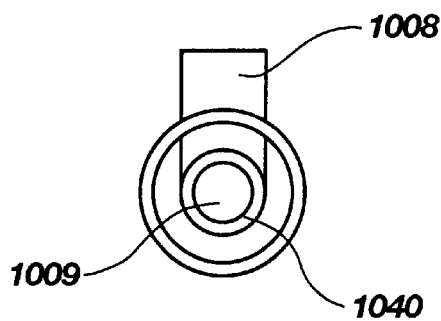
FIG. 10C is an end view of the embodiment of the diverting adapter shown in FIG. 10A.

FIGS. 10A–10C illustrate a further alternative embodiment of the diverting adapter. In this embodiment, the primary passage 800 is defined by cylindrical element 1001. Air flows to chambers 101 and 102 of reservoir 100 through diversion channels 1010 and 1011, respectively. Inlets 1040 and 1041, which communicate with diversion channels 1010 and 1011, respectively, are tubular and run substantially parallel to the longitudinal axis of cylindrical element 1001. A single connector 1008 extends from cylindrical element 1001, substantially perpendicular to its longitudinal axis. Connector 1008 is essentially cylindrical and is split by divider 1009 to form diversion channels 1010 and 1011. Inlet 1040, which communicates with diversion channel 1010, extends in the downstream direction from its junction with channel 1010, while inlet 1041 extends upstream from its junction with channel 1011. Tubes 91 and 92, which connect chambers 101 and 102 of reservoir 100 to diverting adapter 60, are connected to channels 1010 and 1011 by means of an adapter which extends from the connector, which defines half-circular channels 1010 and 1011, to circular outlets compatible with tubes 91 and 92.

Figure 11A:
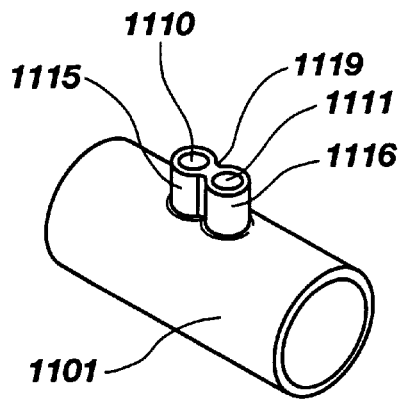
FIG. 11 illustrates a further alternative embodiment of the diverting adapter.
FIG. 11B is a cut-away view of the embodiment of the diverting adapter shown in FIG. 11A.
FIG. 11C is an end view of the embodiment of the diverting adapter shown in FIG. 11A.
Figure 11B:
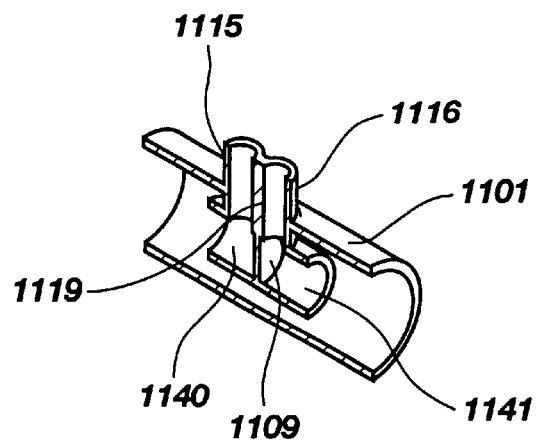
Figure 11C:
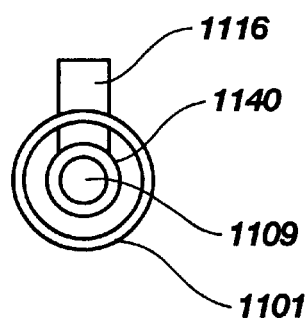

FIGS. 11A–11C illustrate a further alternative embodiment of diverting adapter 60. This embodiment is similar to that shown in FIGS. 10A–10C in that the primary passage 800 is defined by a cylindrical element 1101. Air flow is diverted to chambers 101 and 102 of reservoir 100 by two diversion channels 1110 and 1111, respectively. However, in place of a single connector (1008 in the previously described embodiment), two tubular connectors 1115 and 1116 are used to connect to tubes 91 and 92. Tubular connectors 1115 and 1116 are joined along junction line 1119. Tubes 91 and 92 which connect chambers 101 and 102 to diverting adapter 60 are connected to channels 1110 and 1111, respectively, by sizing them to fit over the tips of connectors 1115 and 1116 and adhesive bonding or welding them thereto. Inlets 1140 and 1141 to diversion channels 1110 and 1111, respectively, are tubular and run parallel to the longitudinal axis of cylindrical element 1101, and substantially perpendicular to the diversion channels. Inlets 1140 and 1141 are separated by divider 1109, which is contiguous with junction line 1119. Inlet 1140, which is in flow communication with diversion channel 1101, extends in the downstream direction from its junction with channel 1101, while inlet 1140 extends upstream from its junction with channel 1111.

Diverting adapter 60, as depicted in FIGS. 8A–11C, may be constructed by injection molding from rigid, sterilizable, polymeric materials, including but not limited to polycarbonate, ABS, and acrylic. The bellows, tubing, and diverting adapter can be preassembled as a unit and sterilized, and be fully disposable after use to prevent cross-patient contamination and associated hazards. Of course, the drive and control mechanisms would be non-disposable, with the drive mechanisms configured to quickly receive and release the bellows or elements thereof.

While the present invention has been described and illustrated in terms of certain specific embodiments, those of ordinary skill in the art will understand and appreciate that it is not so limited. Additions to, deletions from and modifications to these specific embodiments may be effected without departing from the scope of the invention as defined by the claims. Furthermore, features and elements from one specific embodiment may be likewise applied to another embodiment without departing from the scope of the invention as defined herein.

What is claimed is:

1. A gas reservoir system for use in a breathing circuit, comprising:

a first chamber, a second chamber, and a drive mechanism; wherein each said chamber is adapted for containing gas, wherein a volume of each said chamber can be varied, wherein each said chamber has at least one outlet through which said gas is ejected as the volume of said chamber is decreased or drawn in as the volume of said chamber is increased, and wherein the volumes of said first and second chambers are variable by said drive mechanism such that a change in the volume of said first chamber is accompanied by a substantially equal and opposite change in the volume of said second chamber;

a diverting adapter comprising a main flow passage, a first diverting passage communicating with said first chamber through said at least one outlet thereof and said main flow passage, and a second diverting passage communicating with said second chamber through said at least one outlet thereof and said main flow passage; and wherein said gas reservoir system is configured for connection to a primary respiratory path of a said breathing circuit for communication of each of said first and second chambers therewith through said main flow passage of said diverting adapter.

2. A gas reservoir system as in claim 1, wherein said gas reservoir system comprises a bellows-like structure divided into said first and second chambers by an internal wall, wherein said first chamber comprises:

a first end wall;

said internal wall;

a first variable-length side wall connected at a first end thereof to said first end wall and at a second end thereof to said internal wall; and at least one outlet through which gases may enter and exit said first chamber; wherein said second chamber comprises:

a second end wall;

said internal wall;

a second variable-length side wall connected at a first end thereof to said second end wall and at a second end thereof to said internal wall; and at least one outlet through which gases may enter and exit said second chamber; and wherein said first variable-length side wall can be shortened to decrease the volume of said first chamber and lengthened to increase the volume of said first chamber, and wherein said second variable-length side wall can be shortened to decrease the volume of said second chamber and lengthened to increase the volume of said second chamber.

3. A dual chamber gas-reservoir system as in claim 2, wherein said first variable-length side wall and said second variable-length side wall are accordion pleated.

4. A gas reservoir system as in claim 1, comprising:

a rigid-walled cylinder comprising a rigid side wall having a first end and a second end, a first end wall attached to said first end of said rigid side wall and a second end wall attached to said second end of said rigid side wall;

a movable piston wall disposed within said cylinder and dividing the interior of said cylinder into said first chamber and said second chamber;

a piston rod attached to said movable piston wall and passing through an opening in said second end wall to move said movable piston wall within said cylinder;

a first outlet through which gas can flow located in said first chamber; and a second outlet though which gas can flow located in said second chamber;

wherein said movable piston wall forms a substantially gas-tight seal with said rigid side wall to prevent the flow of gas between said first and second chambers, and wherein movement of said inner wall within said cylinder increases the volume of one of said first and second chambers and decreases the volume of the other of said first and second chambers.

5. A gas reservoir system as in claim 1, wherein said first chamber comprises a first fixed end wall in which is located said at least one outlet through which gas can flow, a first movable end wall, and a first variable-length side wall connected at its first end to said first fixed end wall and at its second end to said first movable end wall; wherein said second chamber comprises a second fixed end wall in which is located said at least one outlet through which gas can flow, a second movable end wall; and a second variable-length side wall connected at its first end to said second fixed end wall and at its second end to said second movable end wall; wherein said first variable-length side wall can be shortened to decrease the volume of said first chamber and lengthened to increase the volume of said first chamber; and wherein said second variable-length side wall can be shortened to decrease the volume of said second chamber and lengthened to increase the volume of said second chamber.

6. A gas reservoir system as in claim 5, wherein said first variable-length side wall and said second variable-length side wall are accordion pleated.

7. A gas reservoir system as in claim 1, further comprising:

a first cylinder formed by
a first rigid side wall and
a first end wall attached to one end of said first rigid side wall, and having at least one outlet through which gas can flow;

a first movable piston wall disposed within said first rigid side wall and forming a substantially gas-tight seal with said first rigid side wall;

a first piston rod attached to said first movable piston wall and adapted for moving said first movable piston wall within said first rigid side wall;

a second cylinder formed by
a second rigid side wall and
a second end wall attached to one end of said second rigid side wall,
and having at least one outlet through which gas can flow;

a second movable piston wall disposed within said second rigid side wall and forming a substantially gas-tight seal with said second rigid side wall;

a second piston rod attached to said second moving piston wall and adapted for moving said second moving piston wall within said second rigid side wall;

wherein said first chamber is formed by said first cylinder and said first movable piston wall and said second chamber is formed by said first cylinder and said first movable piston wall.

8. A gas reservoir system as in claim 1, further comprising a first fixed-volume chamber comprising an outlet and an opening;

a first variable-volume chamber disposed within said first fixed-volume chamber, having an outlet and defining said first chamber of said gas reservoir system;

a first tubular member connected to said outlet of said first variable-volume chamber and passing through said opening in said first fixed-volume chamber;

a second fixed-volume chamber comprising an outlet and an opening;

a second variable-volume chamber disposed within said second fixed-volume chamber, having an outlet and defining said second chamber of said gas reservoir system;

a second tubular member connected to said outlet of said second variable-volume chamber and passing through said opening in said second fixed-volume chamber;

wherein a first space is formed between said first fixed-volume chamber and said first variable-volume chamber; wherein a second space is formed between said second fixed-volume chamber and said second variable-volume chamber; wherein said drive mechanism comprises a source for altering pressure within said first and second spaces and selectively communicating with said first space via said outlet of said first fixed-volume chamber and said second space via said outlet of said second fixed-volume chamber; wherein the volume of said first variable-volume chamber is increased by decreasing the pressure within said first space and decreased by increasing the pressure within said first space; and wherein the volume of said second variable-volume chamber is increased by decreasing the pressure within said second space and decreased by increasing the pressure within said second space.

9. A gas reservoir system as in claim 8, wherein said first variable-volume chamber and said second variable-volume chamber are flexible, thin-walled bags.

10. A re-breathing apparatus comprising:

a gas reservoir comprising:
  a first chamber, said first chamber being adapted to contain gas, having a variable volume, and having at least one outlet through which said gas may flow as said volume is increased or decreased;
  a second chamber, said second chamber being adapted to contain gas, having a variable volume, and having at least one outlet through which said gas may flow as said volume is increased or decreased;
  a drive mechanism to increase the volume of one of said first and second chambers by a specified amount and decrease the volume of the other said chamber by substantially said specified amount; and a diverting adapter comprising:
  a main flow passage having a first end and a second end,
  a first diverting passage communicating with said first chamber and said main flow passage; and
  a second diverting passage communicating with said second chamber and said main flow passage;
  wherein said main flow passage of said diverting adapter is configured to communicate with a primary respiratory path of a breathing circuit at said first and second ends thereof.

11. A re-breathing apparatus as in claim 10, wherein said first chamber comprises:

a first end wall comprising said at least one outlet of said first chamber through which said gas can flow;
an internal wall; and
a first variable-length side wall connected at a first end thereof to said first end wall and at a second end thereof to said internal wall;

wherein said second chamber comprises:
  a second end wall comprising said at least one outlet of said second chamber through which said gas can flow;
  said internal wall; and
  a second variable-length side wall connected at a first end thereof to said second end wall and at a second end thereof to said internal wall; and wherein said first variable-length side wall can be shortened to decrease the volume of said first chamber and lengthened to increase the volume of said first chamber, and said second variable-length side wall can be shortened to decrease the volume of said second chamber and lengthened to increase the volume of said second chamber.

12. A re-breathing apparatus as in claim 11, wherein said first variable-length side wall and said second variable-length side wall are accordion pleated.

13. A re-breathing apparatus as in claim 10, wherein said reservoir comprises:

a rigid-walled cylinder comprising a rigid side wall having a first end and a second end, a first end wall attached to said first end of said cylinder and in which is located said at least one outlet through which gas can flow, and a second end wall attached to said second end of said cylinder and in which is located said at least one outlet through which gas can flow;

an movable piston wall disposed within said cylinder and dividing the interior of said cylinder into said first chamber and said second chamber;

a piston rod attached to said movable piston wall and passing through an opening in said second end wall to move said movable piston wall within said rigid-walled cylinder;

wherein said movable piston wall forms a substantially gas-tight seal with said cylinder to prevent the flow of gas between said first and second chambers, and wherein movement of said movable piston wall within said cylinder increases the volume of one of said first and second chambers and decreases the volume of the other of said first and second chambers.

14. A re-breathing apparatus as in claim 10, wherein said first chamber comprises a first fixed end wall comprising said outlet through which gas can flow, a first movable end wall, and a first variable-length side wall connected at its first end to said first fixed end wall and at its second end to said first moving end wall;

wherein said second chamber comprises a second fixed end wall comprising said outlet through which gas can flow, a second movable end wall, and a second variable-length side wall connected at its first end to said second fixed end wall and at its second end to said second moving end wall;

wherein said first variable-length side wall can be shortened to decrease the volume of said first chamber and lengthened to increase the volume of said first chamber; and wherein said second variable-length side wall can be shortened to decrease the volume of said second chamber and lengthened to increase the volume of said second chamber.

15. A re-breathing apparatus as in claim 14, wherein said first variable-length side wall and said second variable-length side wall are accordion pleated.

16. A re-breathing apparatus as in claim 10, wherein said first chamber comprises:

a first rigid side wall;

a first end wall attached to one end of said first rigid side wall and in which is located said at least one outlet through which gas can flow; and a first movable piston wall disposed within said first rigid side wall and forming a substantially gas-tight seal with said first rigid side wall;

and wherein said second chamber comprises:

a second rigid side wall;

a second end wall attached to one end of said second rigid side wall and in which is located said at least one outlet through which gas can flow;

a second movable piston wall slidably disposed within said second rigid side wall and forming a substantially gas-tight seal with said second rigid side wall;

and wherein said drive mechanism comprises a first piston rod attached to said first movable piston wall and adapted for moving said first movable piston wall in within said first rigid side wall and a second piston rod attached to said second movable piston wall and adapted for moving said second movable piston wall within said second rigid side wall.

17. A re-breathing apparatus as in claim 10, wherein said gas reservoir comprises:

a first fixed-volume chamber comprising an outlet and an opening;

a first variable-volume chamber disposed within said first fixed-volume chamber, having an outlet, and defining said first chamber of said gas reservoir;

a first tubular member connected to said outlet of said first variable-volume chamber and passing through said opening in said first fixed-volume chamber;

a second fixed-volume chamber comprising an outlet and an opening;

a second variable-volume chamber disposed within said second fixed-volume chamber, having an outlet, and defining said second chamber of said gas reservoir system;

a second tubular member connected to said outlet of said second variable-volume chamber and passing through said opening in said second fixed-volume chamber;

wherein a first space is formed between said first fixed-volume chamber and said first variable-volume chamber; wherein a second space is formed between said second fixed-volume chamber and said second variable-volume chamber; wherein said drive mechanism comprises a source for selectively altering pressure within said first and second spaces communicating with said first space via said outlet of said first fixed-volume chamber and said second space via said outlet of said second fixed-volume chamber; wherein the volume of said first variable-volume chamber can be decreased by increasing the pressure within said first space and increased by decreasing the pressure within said first space; and wherein the volume of said second variable-volume chamber can be increased by decreasing the pressure within said second space and decreased by increasing the pressure within said second space.

18. A re-breathing apparatus as in claim 17, wherein said first variable-volume chamber and said second variable-volume chamber are flexible thin-walled bags.

19. A breathing circuit comprising:

a primary respiratory path configured for communication with a patient;

an inspiratory hose communicating with said primary respiratory path, through which fresh gases may be provided to said patient;

an expiratory hose communicating with said primary respiratory path, through which expired gases may be vented away from said patient;

a dual-chamber reservoir comprising a first chamber adapted to contain gases and a second chamber adapted to contain gases;

a diverting adapter comprising a main flow passage, a first diverting passage communicating with said first chamber and said main flow passage, and a second diverting passage communicating with said second chamber and said main flow passage, said main flow passage of said diverting adapter disposed in communication with said primary respiratory path; and a drive mechanism;

wherein said first and second chambers are operable in response to said drive mechanism to increase a volume of one of said first and second chambers by an amount and substantially simultaneously decrease a volume of the other of said first and second chambers by substantially said amount.

20. A breathing circuit as in claim 19, wherein said diverting adapter is configured to minimize mixing of gases flowing through said first diverting passage and said second diverting passage.

21. A ventilator circuit as in claim 20, wherein said reservoir further comprises a rigid-walled cylinder comprising:

a rigid side wall having a first end and a second end;

a first end wall attached to said first end of said rigid side wall and having at least one outlet through which gas can flow;

a second end wall attached to said second end of said rigid side wall and having at least one outlet through which gas can flow; and a movable piston wall disposed within said cylinder and dividing the interior of said cylinder into said first chamber and said second chamber;

and wherein said drive mechanism comprises:

a piston rod attached to said movable piston wall and passing through an opening in said second end wall for moving said movable piston wall within said rigid walled cylinder;

wherein said movable piston wall forms a substantially gas-tight seal with said rigid side wall to prevent the flow of gas between said first and second chambers; and wherein movement of said movable piston wall within said cylinder increases the volume of one of said first and second chambers and decreases the volume of the other of said first and second chambers.

22. A breathing circuit as in claim 21, further comprising an actuation mechanism to drive said piston rod to move said movable piston wall within said rigid walled cylinder.

23. A breathing circuit as in claim 20, wherein said first chamber comprises:

a first fixed end wall in which is located said at least one outlet through which gas can flow;

a first movable end wall; and a first variable-length side wall connected at its first end to said first fixed end wall and at its second end to said first movable end wall;

wherein said second chamber comprises:

a second fixed end wall in which is located said at least one outlet through which gas can flow;

a second movable end wall; and a second variable-length side wall connected at its first end to said second fixed end wall and at its second end to said second movable end wall;

wherein said first variable-length side wall can be shortened to decrease the volume of said first chamber and lengthened to increase the volume of said first chamber; and wherein said second variable-length side wall can be shortened to decrease the volume of said second chamber and lengthened to increase the volume of said second chamber.

24. A breathing circuit as in claim 23, wherein said first variable-length side wall and said second variable-length side wall are accordion pleated.

25. A ventilator circuit as in claim 23, further comprising an actuation mechanism to move said first movable end wall with respect to said first fixed end wall and to substantially simultaneously move said second movable end wall with respect to said second fixed end wall, such that said first variable-length side wall can be shortened at substantially the same time as said second variable-length side wall is lengthened, and the said first variable-length side wall can be lengthened at substantially the same time as said second variable-length side wall is shortened.

26. A ventilator circuit as in claim 20, wherein said first chamber comprises:

a first cylinder formed by a first rigid side wall and a first end wall attached to one end of said rigid side wall and in which is located said at least one outlet; and a first movable piston wall disposed within said first cylinder and forming a substantially gas-tight seal with said first rigid side wall;

wherein said second chamber comprises:

a second cylinder formed by a rigid side wall and a second end wall attached to one end of said second rigid side wall and in which is located at least one outlet through which gas can flow; and a second movable piston wall disposed within said second cylinder and forming a substantially gas-tight seal with said second rigid side wall;

and wherein said drive mechanism comprises:

a first piston rod attached to said first movable piston wall and adapted for moving said first movable piston wall within said first rigid walled cylinder and a second piston rod attached to said second movable piston wall and adapted for moving said second movable piston wall within said second rigid walled cylinder.

27. A ventilator circuit as in claim 26, further comprising an actuation mechanism to move said first piston rod to produce a change in the volume of said first chamber and to substantially simultaneously move said second piston rod to produce a change substantially equal and opposite to said change in the volume of said first chamber in the volume of said second chamber.

28. A breathing circuit as in claim 20, wherein said reservoir further comprises:

a first fixed-volume chamber comprising-an outlet and an opening; a first variable-volume chamber having an outlet, said first variable-volume chamber defining said first chamber of said reservoir system;

a first tubular member connected to said outlet of said first variable-volume chamber and passing through said opening in said first fixed-volume chamber;

a second fixed-volume chamber comprising an outlet and an opening;

a second variable-volume chamber having an outlet, said second variable-volume chamber defining said second chamber of said gas reservoir system;

a second tubular member connected to said outlet of said second variable-volume chamber and passing through said opening in said second fixed-volume chamber;

wherein a first space is formed between said first fixed-volume chamber and said first variable-volume chamber; wherein a second space is formed between said second fixed-volume chamber and said second variable-volume chamber; wherein said drive mechanism comprises a source for altering the pressure within said first and second spaces selectively communicating with said first space via said outlet of said first fixed-volume chamber and said second space via said outlet of said second fixed-volume chamber; wherein the volume of said first variable-volume chamber is increased by decreasing the pressure within said first space and decreased by increasing the pressure within said first space; and wherein the volume of said second variable-volume chamber is increased by decreasing the pressure within said second space and decreased by increasing the pressure within said second space.

29. A breathing circuit as in claim 28, wherein said first variable-volume chamber and said second variable-volume chamber are flexible thin-walled bags.

30. A ventilator circuit as in claim 28, further comprising a control mechanism for controlling said source to produce a change in the pressure of said first space while substantially simultaneously producing a change substantially equal and opposite to the change in the pressure of said first space in said second space.

31. A breathing circuit as in claim 19, wherein said first chamber comprises a first end wall in which is located at least one outlet through which gas can flow, an internal wall, and a first variable-length side wall connected at a first end thereof to said first end wall and at a second end thereof to said internal wall;

wherein said second chamber comprises a second end wall in which is located at least one outlet through which gas can flow, said internal wall, and a second variable-length side wall connected at a first end thereof to said second end wall and at a second end thereof to said internal wall; and wherein said first variable-length side wall can be shortened to decrease the volume of said first chamber and lengthened to increase the volume of said first chamber and said second variable-length side wall can be shortened to decrease the volume of said second chamber and lengthened to increase the volume of said second chamber.

32. A breathing circuit as in claim 31, wherein said first variable-length side wall and said second variable-length side wall are accordion pleated.

33. A breathing circuit as in claim 31, further comprising an actuation mechanism for moving said internal wall; wherein said first end wall is held at a fixed distance from said second end wall and said internal wall is moved with respect to said first and second end walls by said actuation mechanism to expand one of said first and second chambers while contracting the other of said first and second chambers.

34. A breathing circuit as in claim 33, wherein said main flow passage comprises:

a cylindrical element having a longitudinal axis and a wall at a diameter d from said longitudinal axis;

a rectangular planar section running parallel to said longitudinal axis at a distance less than said diameter d from said longitudinal axis and intersecting said wall of said cylindrical element along its edges parallel said longitudinal axis;

a first angled wall section, said first angled wall section being planar and intersecting said cylindrical element at an angle θ relative to said longitudinal axis and intersecting said rectangular planar section along an edge perpendicular said longitudinal axis; and a second angled wall section, said second angled wall section being planar and intersecting said cylindrical element at an angle θ relative to said longitudinal axis and intersecting said rectangular planar section along an edge perpendicular said longitudinal axis;

wherein said first diverting passage comprises a first tube connector which connects to said main flow passage at said first angled wall section;

and wherein said second diverting passage comprises a second tube connector which connects to said main flow passage at said second angled wall section.

35. A method of using a re-breathing apparatus, comprising:

drawing a specified volume of expired gases into a first chamber for storage therein as stored expired gases while simultaneously injecting substantially the same volume of gases from a second chamber into a breathing circuit, said expired gases having been expired into said breathing circuit by a patient during an expiratory breath; and during a first inspiration of re-breathing, injecting said stored expired gases from said first chamber into said breathing circuit for immediate re-breathing thereof by said patient while simultaneously drawing gases from said breathing circuit into said second chamber.

36. A method in accordance with claim 35, wherein said expiratory breath is a final expiratory breath prior to a start of re-breathing.

37. A diverting airway adapter for use in a re-breathing circuit, comprising:

main flow passage having a first end and a second end;

a first diverting passage for communicating between said main flow passage and a first chamber of a gas reservoir system of a re-breathing circuit; and a second diverting passage for communicating between said main flow passage and a second chamber of said gas reservoir system of said re-breathing circuit;

wherein said diverting airway adapter is configured for connection into a primary respiratory path of said re-breathing circuit at said first and second ends of said main flow passage, wherein said first diverting passage provides for a flow of gases between said primary respiratory path and a first re-breathing circuit connection to said first chamber, and wherein said second diverting passage provides for a flow of gases between said primary respiratory path and a second re-breathing circuit connection to said second chamber.

38. A diverting airway adapter in accordance with claim 37, wherein said main flow passage comprises:

a cylindrical element having a longitudinal axis and a wall at a diameter d from said longitudinal axis;

a rectangular planar section running parallel to said longitudinal axis at a distance less than said diameter d from said longitudinal axis, and intersecting said wall of said cylindrical element along its edges parallel said longitudinal axis;

a first angled wall section, said first angled wall section being planar and intersecting said cylindrical element at an angle θ relative to said longitudinal axis and intersecting said rectangular planar section along an edge perpendicular to said longitudinal axis; and a second angled wall section, said second angled wall section being planar and intersecting said cylindrical element at an angle θ relative to said longitudinal axis and intersecting said rectangular planar section along an edge perpendicular to said longitudinal axis;

wherein said first diverting passage is defined by a first tube connector which connects to said main flow passage at said first angled wall section; and wherein said second diverting passage is defined by a second tube connector which connects to said main flow passage at said second angled wall section.

39. A diverting airway adapter in accordance with claim 37, wherein said main flow passage comprises:

a cylindrical element having a downstream end further from a patient and an upstream end closer to said patient;

a primary flow tube, said primary flow tube inside and substantially co-axial with said cylindrical element;

an annular support element, said annular support element attached at its periphery to said cylindrical element and at its inner edge to said primary flow tube, so that said primary flow tube is supported and fixed with respect to said cylindrical element;

a first tube connector connecting to said cylindrical element downstream from said annular support element and communicating with the space between said cylindrical element and said primary flow tube downstream of said annular support element; and a second tube connector connecting to said cylindrical element upstream from said annular support element and communicating with the space between said cylindrical element and said primary flow tube upstream of said annular support element;

wherein said first diverting passage is defined by said first tube connector and said second diverting adapter is defined by said second tube connector.

40. A diverting airway adapter in accordance with claim 37, comprising:

a cylindrical element having longitudinal axis, a downstream end further from a patient, and an upstream end closer to a patient;

a tubular connector connected to and extending substantially perpendicularly from said cylindrical element;

an internal divider dividing said tubular connector into a first diversion channel and a second diversion channel;

a first tubular inlet, substantially parallel to said longitudinal axis of said cylindrical element and communicating with, substantially perpendicular to, and extending in a downstream direction from said first diversion channel;

a second tubular inlet, substantially parallel to said longitudinal axis of said cylindrical element and communicating with, substantially perpendicular to and extending in a downstream direction from said second diversion channel.

41. A diverting airway adapter in accordance with claim 37, comprising:

a cylindrical element defining said main flow passage, having a longitudinal axis, a downstream end further from a patient, and an upstream end closer to said patient;

a first tubular connector defining said first diverting passage, connected to and extending substantially perpendicularly from said cylindrical element;

a second tubular connector defining said second diverting passage, connected to and extending substantially perpendicularly from said cylindrical element, adjacent to and upstream from said first tubular connector; and a first inlet, running substantially parallel to said longitudinal axis of said cylindrical element on the inside of said cylindrical element and communicating with, essentially perpendicular to, and extending in a downstream direction from said first diverting passage; and a second inlet, running substantially parallel to said longitudinal axis of said cylindrical element on the inside of said cylindrical element and communicating with, essentially perpendicular to, and extending in a downstream direction from said second diverting passage.

* * * * *